United States Patent
Richelsoph

(10) Patent No.: US 7,655,045 B2
(45) Date of Patent: *Feb. 2, 2010

(54) ARTIFICIAL INTERVERTEBRAL DISC

(75) Inventor: Marc Richelsoph, Bartlett, TN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/494,315

(22) Filed: Jul. 27, 2006

(65) Prior Publication Data

US 2006/0265071 A1    Nov. 23, 2006

Related U.S. Application Data

(63) Continuation of application No. 10/430,861, filed on May 6, 2003, now Pat. No. 7,105,024.

(51) Int. Cl.
    *A61F 2/44* (2006.01)
(52) U.S. Cl. ............... 623/17.13; 623/17.14; 623/17.15
(58) Field of Classification Search ............. 623/17.13, 623/17.11, 17.12, 17.14, 17.15, 17.16; 606/61
    See application file for complete search history.

(56) References Cited

U.S. PATENT DOCUMENTS

| | | | |
|---|---|---|---|
| 3,426,364 A | 2/1969 | Lumb | |
| 3,867,728 A | 2/1975 | Stubstad et al. | |
| 3,875,595 A | 4/1975 | Froning | |
| 4,309,777 A | 1/1982 | Patil | |
| 4,759,766 A | 7/1988 | Buettner-Janz et al. | |
| 4,759,769 A * | 7/1988 | Hedman et al. | 623/17.13 |
| 4,848,555 A | 7/1989 | Riese et al. | |
| 4,863,476 A | 9/1989 | Shepperd | |
| 4,863,477 A | 9/1989 | Monson | |
| 4,911,718 A | 3/1990 | Lee et al. | |
| 5,002,576 A | 3/1991 | Fuhrmann et al. | |
| 5,037,438 A | 8/1991 | Davidson | |
| 5,119,531 A | 6/1992 | Berger et al. | |
| 5,122,130 A | 6/1992 | Keller | |
| 5,123,926 A | 6/1992 | Pisharodi | |
| 5,192,327 A | 3/1993 | Brantigan | |

(Continued)

FOREIGN PATENT DOCUMENTS

DE        900094        12/1953

(Continued)

OTHER PUBLICATIONS

Partial European Search Report; Aug. 22, 2005; Berlin.

(Continued)

*Primary Examiner*—Pedro Philogene
(74) *Attorney, Agent, or Firm*—RatnerPrestia

(57) ABSTRACT

An artificial intervertebral disc includes housing members including spaced inner surfaces facing each other and oppositely facing outer surfaces for engaging spaced apart vertebral surfaces. Bearing surfaces extend from each of the inner surfaces for engaging each other while allowing for low friction and compression resistant movement of the housing members relative to each other while under compression. Load sharing pads are disposed between the inner surfaces and about at least a portion of the bearing surfaces for sharing absorption compressive loads with the bearing surfaces while limiting the relative movement of the housing members.

22 Claims, 13 Drawing Sheets

U.S. PATENT DOCUMENTS

| | | | |
|---|---|---|---|
| 5,201,101 A | 4/1993 | Rouser et al. | |
| 5,236,460 A | 8/1993 | Barber | |
| 5,258,031 A | 11/1993 | Salib | |
| 5,306,308 A | 4/1994 | Gross et al. | |
| 5,314,477 A | 5/1994 | Marnay | |
| 5,370,697 A * | 12/1994 | Baumgartner | 623/17.15 |
| 5,401,269 A | 3/1995 | Buttner-Janz et al. | |
| 5,425,773 A | 6/1995 | Boyd et al. | |
| 5,507,816 A | 4/1996 | Bullivant | |
| 5,534,030 A | 7/1996 | Navarro et al. | |
| 5,545,227 A | 8/1996 | Davidson et al. | |
| 5,549,689 A | 8/1996 | Epstein et al. | |
| 5,556,431 A | 9/1996 | Büttner-Janz | |
| 5,562,738 A | 10/1996 | Boyd et al. | |
| 5,674,294 A | 10/1997 | Bainville et al. | |
| 5,674,296 A | 10/1997 | Bryan et al. | |
| 5,676,635 A | 10/1997 | Levin | |
| 5,676,701 A | 10/1997 | Yuan et al. | |
| 5,683,465 A | 11/1997 | Shinn et al. | |
| 5,702,449 A | 12/1997 | McKay | |
| 5,782,830 A | 7/1998 | Farris | |
| 5,782,832 A | 7/1998 | Larsen et al. | |
| 5,824,094 A | 10/1998 | Serhan et al. | |
| 5,827,328 A | 10/1998 | Buttermann | |
| 5,865,846 A | 2/1999 | Bran et al. | |
| 5,888,226 A | 3/1999 | Rogozinski | |
| 5,888,227 A | 3/1999 | Cottle | |
| 5,893,889 A | 4/1999 | Harrington | |
| 5,989,291 A | 11/1999 | Ralph et al. | |
| 6,001,130 A | 12/1999 | Bryan | |
| 6,013,103 A | 1/2000 | Kaufman et al. | |
| 6,019,792 A | 2/2000 | Cauthen | |
| 6,019,793 A | 2/2000 | Perren et al. | |
| 6,039,763 A | 3/2000 | Shelokov | |
| 6,063,121 A | 5/2000 | Xavier et al. | |
| 6,083,225 A | 7/2000 | Winslow et al. | |
| 6,113,637 A | 9/2000 | Gill et al. | |
| 6,113,639 A | 9/2000 | Ray et al. | |
| 6,127,597 A | 10/2000 | Beyar et al. | |
| 6,139,579 A | 10/2000 | Steffee et al. | |
| 6,146,421 A | 11/2000 | Gordon et al. | |
| 6,156,067 A | 12/2000 | Bryan et al. | |
| 6,162,252 A | 12/2000 | Kuras et al. | |
| 6,176,881 B1 | 1/2001 | Schär et al. | |
| 6,193,757 B1 | 2/2001 | Foley et al. | |
| 6,200,322 B1 | 3/2001 | Branch et al. | |
| 6,206,923 B1 | 3/2001 | Boyd et al. | |
| 6,210,442 B1 | 4/2001 | Wing et al. | |
| 6,231,609 B1 | 5/2001 | Mehdizadeh | |
| 6,277,149 B1 | 8/2001 | Boyle et al. | |
| 6,296,664 B1 | 10/2001 | Middleton | |
| 6,669,732 B2 | 2/2002 | Serhan et al. | |
| 6,367,128 B1 | 4/2002 | Galkiewicz et al. | |
| 6,368,350 B1 | 4/2002 | Erickson et al. | |
| 6,395,032 B1 | 5/2002 | Gauchet | |
| 6,419,704 B1 | 7/2002 | Ferree | |
| 6,419,706 B1 | 7/2002 | Graf | |
| 6,443,987 B1 | 9/2002 | Bryan | |
| 6,443,990 B1 | 9/2002 | Aebi et al. | |
| 6,468,310 B1 | 10/2002 | Ralph et al. | |
| 6,491,726 B2 | 12/2002 | Pappas | |
| 6,494,915 B1 | 12/2002 | Villar Gonzalez et al. | |
| 6,723,127 B2 | 1/2003 | Ralph et al. | |
| 6,517,580 B1 | 2/2003 | Ramadan et al. | |
| 6,520,996 B1 | 2/2003 | Manasas et al. | |
| 6,524,341 B2 | 2/2003 | Läng et al. | |
| 6,527,804 B1 | 3/2003 | Gauchet et al. | |
| 6,527,806 B2 * | 3/2003 | Ralph et al. | 623/17.16 |
| 6,530,955 B2 | 3/2003 | Boyle et al. | |
| 6,533,818 B1 | 3/2003 | Weber et al. | |
| 6,540,785 B1 | 4/2003 | Gill et al. | |
| 6,673,113 B2 | 4/2003 | Ralph et al. | |
| 6,558,424 B2 | 5/2003 | Thalgott | |
| 6,562,072 B1 | 5/2003 | Fuss et al. | |
| 6,572,653 B1 | 6/2003 | Simonson | |
| 6,575,899 B1 | 6/2003 | Foley et al. | |
| 6,579,320 B1 | 6/2003 | Gauchet et al. | |
| 6,579,321 B1 | 6/2003 | Gordon et al. | |
| 6,582,466 B1 | 6/2003 | Gauchet | |
| 6,582,468 B1 | 6/2003 | Gauchet | |
| 6,607,558 B2 | 8/2003 | Kuras | |
| 6,610,092 B2 | 8/2003 | Ralph et al. | |
| 6,613,090 B2 | 9/2003 | Fuss et al. | |
| 6,626,943 B2 | 9/2003 | Eberlein et al. | |
| 6,706,068 B2 | 10/2003 | Ferree | |
| 6,645,248 B2 | 11/2003 | Casutt | |
| 6,645,249 B2 | 11/2003 | Ralph et al. | |
| 6,656,224 B2 | 12/2003 | Middleton | |
| 6,666,889 B1 | 12/2003 | Commarmond | |
| 6,669,730 B2 | 12/2003 | Ralph et al. | |
| 6,682,562 B2 | 1/2004 | Viart et al. | |
| 6,723,097 B2 | 1/2004 | Fraser et al. | |
| 6,719,796 B2 | 4/2004 | Cohen et al. | |
| 6,726,720 B2 | 4/2004 | Ross et al. | |
| 6,733,532 B1 | 5/2004 | Gauchet et al. | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,740,119 B2 | 5/2004 | Ralph et al. | |
| 6,758,861 B2 | 7/2004 | Ralph et al. | |
| 6,764,515 B2 | 7/2004 | Ralph et al. | |
| 6,770,094 B2 | 8/2004 | Fehling et al. | |
| 6,770,095 B2 | 8/2004 | Grinberg et al. | |
| 6,793,678 B2 | 9/2004 | Hawkins | |
| 6,802,867 B2 | 10/2004 | Manasas et al. | |
| 6,827,740 B1 | 12/2004 | Michelson | |
| 6,918,934 B2 * | 7/2005 | Ralph et al. | 623/17.14 |
| 6,936,071 B1 | 8/2005 | Marnay et al. | |
| 6,984,245 B2 | 1/2006 | McGahan et al. | |
| 6,986,789 B2 | 1/2006 | Schultz et al. | |
| 7,001,432 B2 | 2/2006 | Keller et al. | |
| 7,105,024 B2 | 9/2006 | Richelsoph | |
| 7,156,876 B2 | 1/2007 | Moumene et al. | |
| 7,179,294 B2 | 2/2007 | Eisermann et al. | |
| 7,198,644 B2 | 4/2007 | Schultz et al. | |
| 7,291,173 B2 | 11/2007 | Richelsoph et al. | |
| 7,326,250 B2 * | 2/2008 | Beaurain et al. | 623/17.14 |
| 2001/0016773 A1 | 8/2001 | Serhan et al. | |
| 2002/0022887 A1 | 2/2002 | Huene | |
| 2002/0035400 A1 | 3/2002 | Bryan et al. | |
| 2002/0107573 A1 | 8/2002 | Steinberg | |
| 2002/0111681 A1 | 8/2002 | Ralph et al. | |
| 2003/0009223 A1 | 1/2003 | Fehling et al. | |
| 2003/0014112 A1 | 1/2003 | Ralph et al. | |
| 2003/0040802 A1 | 2/2003 | Errico et al. | |
| 2003/0055427 A1 | 3/2003 | Graf | |
| 2003/0065395 A1 | 4/2003 | Ralph et al. | |
| 2003/0069586 A1 | 4/2003 | Errico et al. | |
| 2003/0069640 A1 | 4/2003 | Ferreira et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0078590 A1 | 4/2003 | Errico et al. | |
| 2003/0078663 A1 | 4/2003 | Ralph et al. | |
| 2003/0078666 A1 | 4/2003 | Ralph et al. | |
| 2003/0135277 A1 | 7/2003 | Bryan et al. | |
| 2003/0176923 A1 | 9/2003 | Keller et al. | |

| | | | | | |
|---|---|---|---|---|---|
| 2003/0187454 A1 | 10/2003 | Gill et al. | DE | 203 11 400 | 10/2003 |
| 2003/0187506 A1 | 10/2003 | Ross et al. | DE | 20313183 | 10/2003 |
| 2003/0191534 A1 | 10/2003 | Viart et al. | DE | 697 22 244 | 12/2003 |
| 2003/0220691 A1 | 11/2003 | Songer et al. | DE | 203 15 611 | 1/2004 |
| 2003/0229355 A1 | 12/2003 | Keller | DE | 203 15 613 | 1/2004 |
| 2003/0229358 A1 | 12/2003 | Errico et al. | DE | 20 2004 009 542 | 9/2004 |
| 2003/0233146 A1 | 12/2003 | Grinberg et al. | DE | 20 2004 014 119 | 12/2004 |
| 2003/0236520 A1 | 12/2003 | Lim et al. | EP | 0 282 161 | 9/1988 |
| 2003/0236571 A1 | 12/2003 | Ralph et al. | EP | 0 282 161 A1 | 9/1988 |
| 2004/0002761 A1 | 1/2004 | Rogers et al. | EP | 0 471 821 | 2/1992 |
| 2004/0002762 A1 | 1/2004 | Hawkins | EP | 0 560 141 | 9/1993 |
| 2004/0010316 A1 | 1/2004 | William et al. | EP | 94/04100 | 3/1994 |
| 2004/0024462 A1 | 2/2004 | Ferree et al. | EP | 0 634 157 | 1/1995 |
| 2004/0034420 A1 | 2/2004 | Errico et al. | EP | 0 747 025 | 12/1996 |
| 2004/0034421 A1 | 2/2004 | Errico et al. | EP | 0 948 299 | 10/1999 |
| 2004/0034422 A1 | 2/2004 | Errico et al. | EP | 0955021 | 11/1999 |
| 2004/0034424 A1 | 2/2004 | Errico et al. | EP | 1 002 500 | 5/2000 |
| 2004/0034426 A1 | 2/2004 | Errico et al. | EP | 1057462 | 12/2000 |
| 2004/0059318 A1 | 3/2004 | Zhang et al. | EP | 1 103 237 A2 | 5/2001 |
| 2004/0073310 A1 | 4/2004 | Moumene et al. | EP | 1 124 509 | 8/2001 |
| 2004/0073312 A1 | 4/2004 | Eisermann et al. | EP | 1344508 | 3/2002 |
| 2004/0078079 A1 | 4/2004 | Foley | EP | 1 103 237 A3 | 4/2002 |
| 2004/0083000 A1 | 4/2004 | Keller et al. | EP | 1 250 898 | 10/2002 |
| 2004/0093088 A1 | 5/2004 | Ralph et al. | EP | 1250898 | 10/2002 |
| 2004/0098130 A1 | 5/2004 | Ralph et al. | EP | 1263352 | 12/2002 |
| 2004/0098131 A1 | 5/2004 | Bryan et al. | EP | 1 344 507 | 9/2003 |
| 2004/0102849 A1 | 5/2004 | Ralph et al. | EP | 1 344 508 | 9/2003 |
| 2004/0111156 A1 | 6/2004 | Ralph et al. | EP | 1374808 | 1/2004 |
| 2004/0117021 A1 | 6/2004 | Biedermann et al. | EP | 1421922 | 5/2004 |
| 2004/0117022 A1 | 6/2004 | Marnay et al. | EP | 1188423 | 9/2004 |
| 2004/0133278 A1 | 7/2004 | Marino et al. | EP | 1 475 059 | 11/2004 |
| 2004/0133281 A1 | 7/2004 | Khandkar et al. | FR | 2 694 882 | 2/1994 |
| 2004/0143331 A1 | 7/2004 | Errico et al. | FR | 2 730 159 | 8/1996 |
| 2004/0143332 A1 | 7/2004 | Krueger et al. | FR | 2 799 638 A1 | 10/1999 |
| 2004/0148027 A1 | 7/2004 | Errico et al. | FR | 2 718 635 | 1/2001 |
| 2004/0158325 A1 | 8/2004 | Errico et al. | FR | 2 799 116 | 4/2001 |
| 2004/0158328 A1 | 8/2004 | Eisermann | FR | 2 824 261 | 11/2002 |
| 2004/0167534 A1 | 8/2004 | Errico et al. | JP | 06178787 | 6/1994 |
| 2004/0167536 A1 | 8/2004 | Errico et al. | WO | WO 94/04100 | 3/1994 |
| 2004/0167537 A1 | 8/2004 | Errico et al. | WO | WO 95/26697 | 10/1995 |
| 2004/0167626 A1 | 8/2004 | Geremakis et al. | WO | WO 99/11203 | 3/1999 |
| 2004/0170342 A1 | 9/2004 | Galkiewicz | WO | WO 99/05995 | 11/1999 |
| 2004/0193158 A1 | 9/2004 | Lim et al. | WO | WO 00/04851 | 2/2000 |
| 2004/0220582 A1 | 11/2004 | Keller | WO | WO 00/13619 | 3/2000 |
| 2004/0220668 A1 | 11/2004 | Eisermann et al. | WO | WO 00/23015 | 4/2000 |
| 2004/0220670 A1 | 11/2004 | Eisermann et al. | WO | WO 00/35385 | 6/2000 |
| 2004/0220677 A1 | 11/2004 | Delfosse et al. | WO | WO 00/53127 | 9/2000 |
| 2004/0225362 A1 | 11/2004 | Richelsoph | WO | WO 00/64385 | 11/2000 |
| 2004/0225363 A1 | 11/2004 | Richelsoph | WO | WO 01/01893 A1 | 1/2001 |
| 2004/0225364 A1 | 11/2004 | Richelsoph et al. | WO | WO 01/01895 | 1/2001 |
| 2004/0225365 A1 | 11/2004 | Eisermann et al. | WO | WO 01/18931 | 3/2001 |
| 2004/0225366 A1 | 11/2004 | Eisermann et al. | WO | WO 01/19295 | 3/2001 |
| 2004/0243238 A1 | 12/2004 | Arnin et al. | WO | WO 01/64140 | 9/2001 |
| 2004/0243240 A1 | 12/2004 | Beaurain et al. | WO | WO 01/68003 | 9/2001 |
| 2004/0249462 A1 | 12/2004 | Huang | WO | WO 01/93785 | 12/2001 |
| 2005/0033438 A1 | 2/2005 | Schultz et al. | WO | WO 01/93786 | 12/2001 |
| 2005/0043803 A1 | 2/2005 | Schultz et al. | WO | WO 02/080818 | 10/2002 |
| 2005/0080487 A1 | 4/2005 | Schultz et al. | WO | WO 02/089701 | 11/2002 |
| 2005/0080488 A1 | 4/2005 | Schultz | WO | WO 03/003952 | 1/2003 |
| 2006/0036326 A1 | 2/2006 | Baumgartner et al. | WO | WO 03/007779 | 1/2003 |
| | | | WO | WO 03/007780 | 1/2003 |
| FOREIGN PATENT DOCUMENTS | | | WO | WO 03/028595 | 4/2003 |
| | | | WO | WO 03/039400 | 5/2003 |
| DE | 2 263 842 | 12/1972 | WO | WO 03/047472 | 6/2003 |
| DE | 30 23 353 | 4/1981 | WO | WO 03/075803 | 9/2003 |
| DE | 239 524 | 1/1986 | WO | WO 03/075804 | 9/2003 |
| DE | 90 00 094 | 1/1990 | WO | WO 03/084449 | 10/2003 |
| DE | 197 10 392 | 7/1999 | WO | WO 03/090648 | 11/2003 |
| DE | 29911422 | 8/1999 | WO | WO 03/094806 A1 | 11/2003 |
| DE | 198 16 832 | 1/2000 | WO | WO 03/099172 | 12/2003 |
| DE | 101 52 567 | 5/2003 | WO | WO 2004/016205 | 2/2004 |
| DE | 203 10 433 | 9/2003 | WO | WO 2004/019828 | 3/2004 |
| DE | 20310432 | 9/2003 | WO | WO 2004/026186 | 4/2004 |

| WO | WO 2004/041129 | 5/2004 |
| WO | WO 2004/041131 | 5/2004 |
| WO | WO 22004/039285 | 5/2004 |
| WO | WO 2004/054475 | 7/2004 |
| WO | WO 2004/054476 | 7/2004 |
| WO | WO 2004/054478 | 7/2004 |
| WO | WO 2004/054480 | 7/2004 |
| WO | WO 2004/073561 | 10/2004 |
| WO | WO 2004/084774 | 10/2004 |

OTHER PUBLICATIONS

Szpalski, Marek, Gunzburg, Robert, and Mayer, Michael, "Spine Arthroplasty: A Historical Review", Eur Spine J (2002), 11 (Suppl. 2), pp. S65-S84.

Article from the Burton Report, "Artificial Discs", 5 pages, website at http://www.burtonreport.com/infspine/surgartificialdiscs.htm.

Traynelis, M.D., Vincent, and Haid, Jr., M.D., Regis W., "Spinal Disc Replacement: the Development of Artificial Discs", 12 pages.

Bao, Ph.D., Qi-Bin, and Yuan, M.D., Hansen A., "Artificial Disc Technology", Neurosurg Focus 9(4), 2000, 2000 American Association of Neurological Surgeons, 12 pages.

German Search Report for European Application EP 04 72 6859.4; Completed Sep. 21, 2006; Examiner Stach, Rainer—Berlin; Issued Oct. 4, 2006.

PCT Search Report for PCT EP/2004/006956; Completed Oct. 22, 2004, Mailed Nov. 4, 2004.

European Search Report for European Application No. EP-07018677 dated Feb. 20, 2008.

U.S Appl. No. 11/494,316 of Richelsoph filed Jul. 27, 2006.

U.S Appl. No. 10/653,540 of Richelsoph et al. filed Sep. 2, 2003.

U.S Appl. No. 11/875,413 of Richelsoph et al. filed Oct. 19, 2007.

U.S Appl. No. 10/867,837 of Richelsoph filed Jun. 15, 2004.

U.S Appl. No. 11/153,798 of Schneid et al. filed Jun. 15, 2005.

U.S Appl. No. 10/791,050 of Lo et al. filed Mar. 2, 2004 (Abandoned).

U.S Appl. No. 10/879,449, of Schultz et al. filed Jun. 29, 2004.

U.S Appl. No. 10/882,618, of Schultz filed Jun. 30, 2004.

U.S Appl. No. 10/885,370, of Schultz et al. filed Jul. 6, 2004.

* cited by examiner

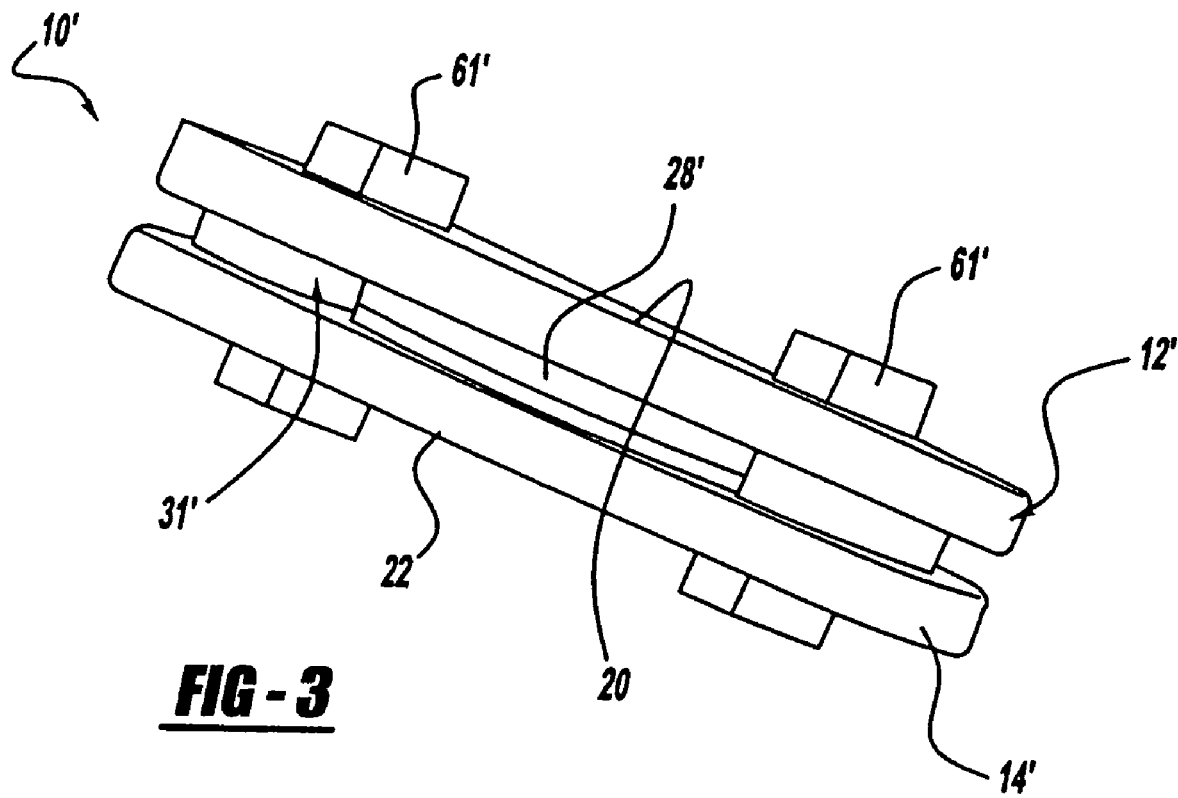
FIG - 3
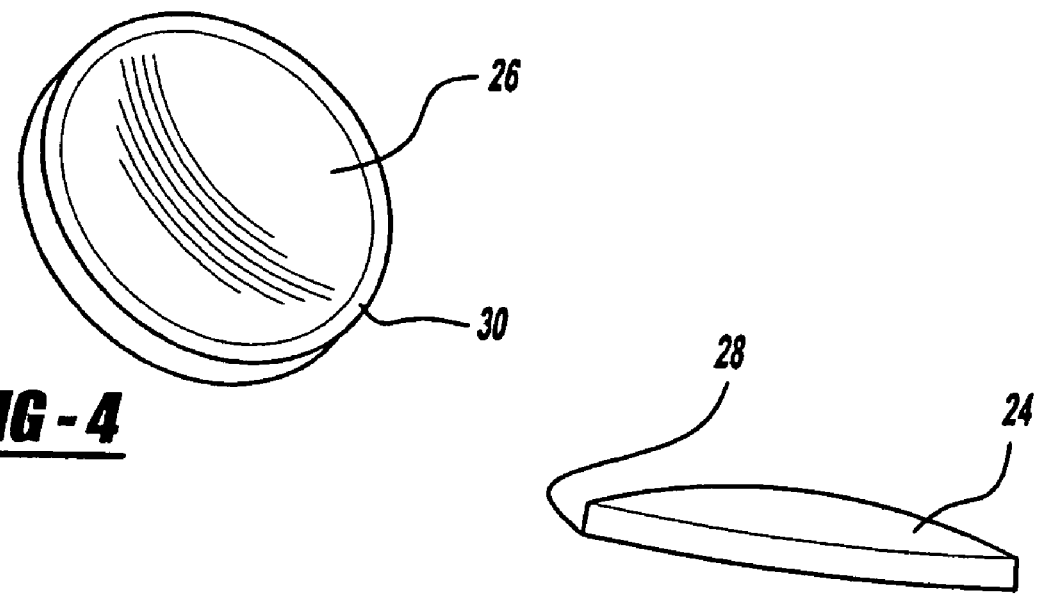
FIG - 4
FIG - 5

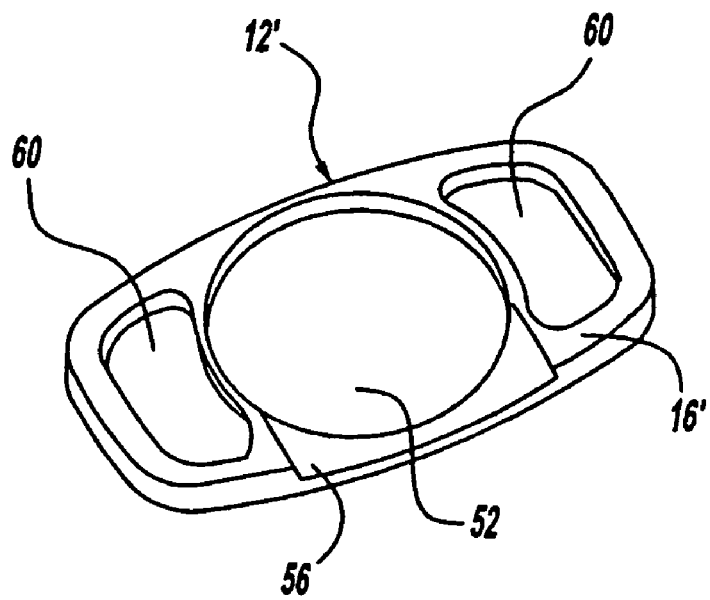
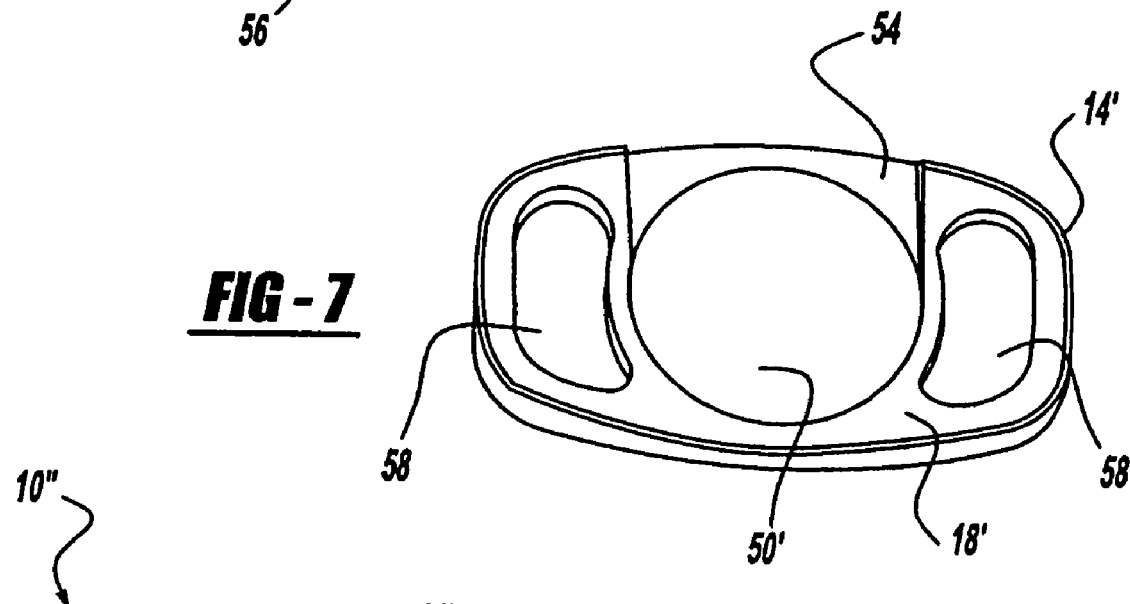
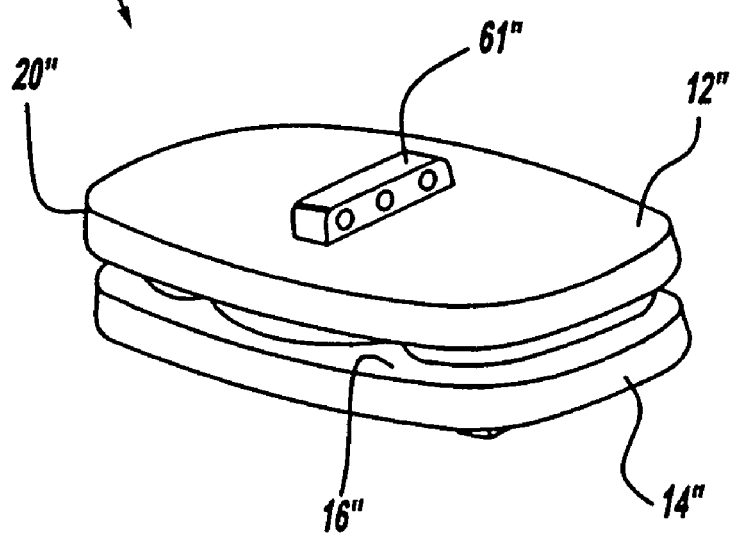

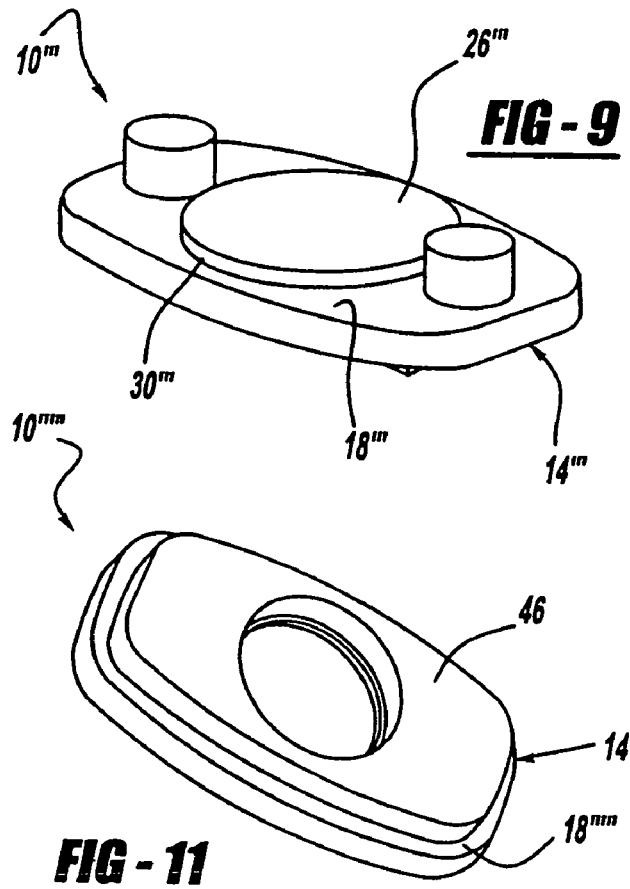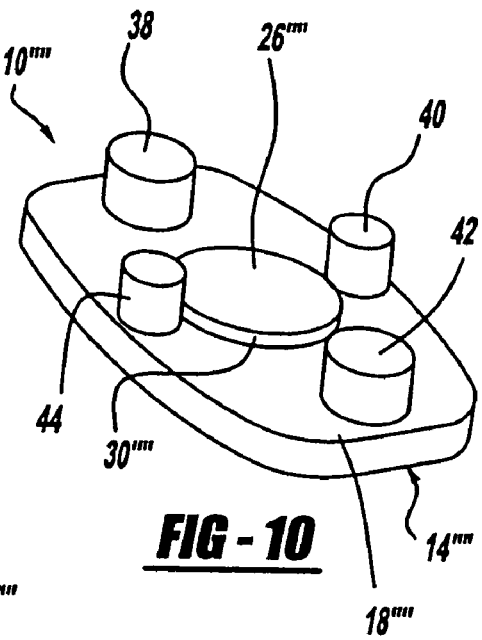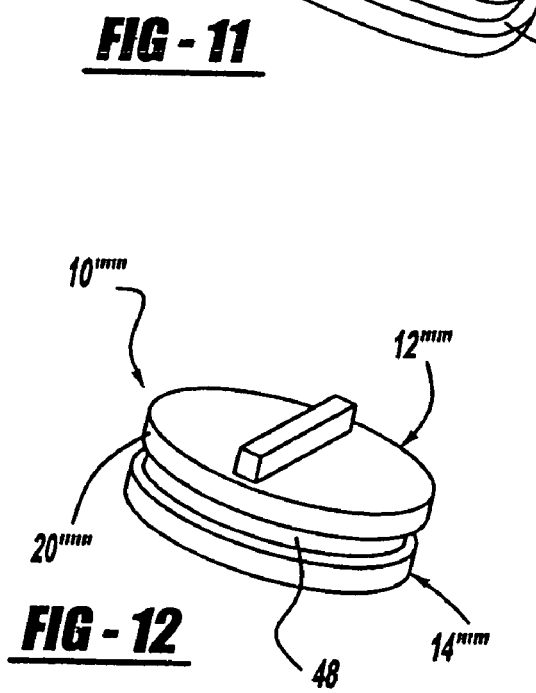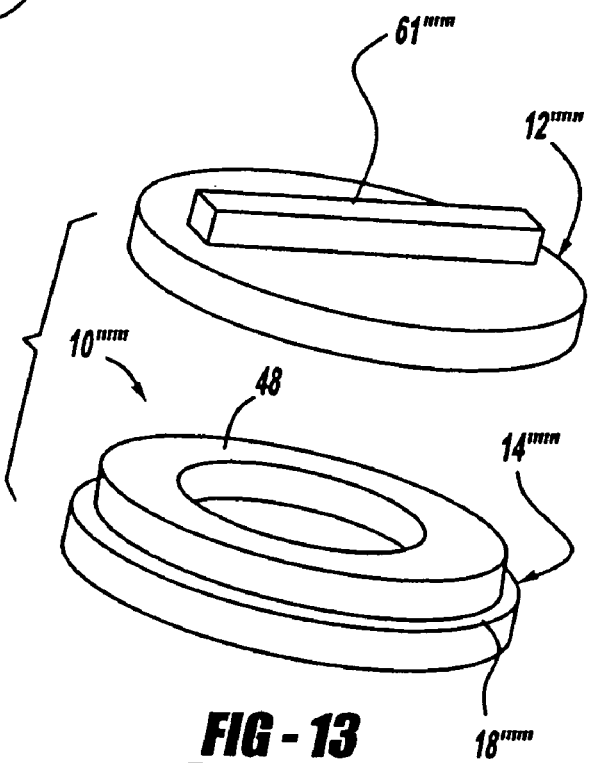

ARTIFICIAL INTERVERTEBRAL DISC

This application is a Continuation of U.S. application Ser. No. 10/430,861 filed May 6, 2003 now U.S. Pat. No. 7,105,024.

BACKGROUND OF THE INVENTION

1. Technical Field

The present invention relates generally to a spinal implant assembly for implantation into the intervertebral space between adjacent vertebral bones to provide stabilization and continued postoperative flexibility and proper anatomical motion. More specifically, the present invention relates to an artificial intervertebral disc, sometimes referred to as an intervertebral spacer device, for functioning as a load sharing and bearing device for replacement of the damaged, decayed, or otherwise nonfunctioning intervertebral disc.

2. Background of the Invention

The spine is a complex structure consisting of multiple flexible levels. Each level consists of a system of joints defined by adjacent vertebral bones. The system of joints includes intervertebral discs, which are a two-part structure. The disc consists of a nucleus and an annulus. The system allows motion while the facet joints add posterior stabilization to the spinal column. The disc allows motion and cushioning to the joint.

The complex system of the joint is subjected to varying loads and problems over time, including disc degeneration due to a variety of reasons. Disc degeneration can be attributed to aging, damage due to excessive loading, trauma, and other anatomical issues. Facet joints of the structure can be compromised due to the same reasons, as well as due to arthritic changes. Severe joint degeneration and failure can often cause sufficient pain to require surgical intervention.

The current standard method of treatment for severe pain caused by spine joint problems is fusion at the damaged level of the spine. The treatment, when successful, fuses the damaged section into a single mass of bone. The fusion of the joint eliminates motion of the joint, thereby reducing or eliminating pain at that level. Success rates for pain elimination are very high for this method of treatment. However, since the entire spine works as a system, fusion results in complications.

Elimination of motion at the spine alters the biomechanics of the spine at every other level. If one level is fused, then loads are absorbed by one less disc into a system not designed for such change. Thus, the remaining discs must redistribute loads, each disc absorbing a greater load. In addition, the spine flexes to absorb loads. A fusion alters the means by which the spine flexes, which also increases the loads on the remaining healthy discs. In turn, it is well understood that a complication of fusion is that additional fusions may be required in the future as the other discs deteriorate due to the altered biomechanics of the spine. In other words, short-term pain relief is exchanged for long-term alterations of the spine, which, in turn, usually require further surgery.

There are numerous prior art patents addressing the issue of disc replacement. The U.S. Pat. Nos. 6,443,987 B1 and 6,001,130, both to Bryan, disclose polymer composite structures for cushioning intervertebral loads. The U.S. Pat. No. 5,258,031 to Salib, et al. and U.S. Pat. No. 5,314,477 to Marnay disclose ball and socket type implants addressing the issue of intervertebral mobility. These patents are exemplary of a first approach using an elastomer as a motion and dampening structure and a second approach utilizing a ball and socket joint to create a moving pivot joint. There are many variations on these concepts, which include mechanical springs and more complex structural mechanisms. A significant portion of the prior art addresses the issues of intervertebral motion but do not address anatomical loading considerations.

The current state of prior art artificial intervertebral discs are associated with various problems. For example, a number of implants constructed from polymers are of insufficient strength to work effectively in the higher loading areas, such as the lumbar spine. Such polymers often take compressive sets so that the original height of the implant decreases over time. A surgeon must either compensate for the compression by initially using a larger polymer prosthesis and estimate compression or use the appropriately sized polymer prosthesis and later surgically replace the same once the irreversible compression of the prosthesis is unacceptable.

Implants constructed with ball and socket joints severely restrict or eliminate shock cushioning effect of a normal disc. This implant can provide motion, but biomechanically, the ball and socket joint negatively affects other healthy discs of the spine. The result can be long-term problems at other levels of the spine, as seen with the current treatment of fusion.

Other implants, not discussed above, utilize bearing surfaces usually having polyethylene bearing against metal interfaces. Polyethylene as a bearing surface is problematic in large joint replacement due to the wear properties of the material. Since artificial discs are intended to be implanted over long periods of time, such wear can be highly damaging to surrounding tissue and bone.

In view of the above, it is desirable to provide a solution to intervertebral disc replacement that restores motion to the damaged natural disc area while allowing for motion as well as cushioning and dampening, similar to the naturally occurring disc. In addition, it is preferable to allow such motion, cushioning, and dampening while preventing a polymer or elastomeric material from experiencing the relatively high compressive loads seen in the spine. It is also preferable to allow a bearing surface to share the spinal loads with the polymer and elastomeric material. Finally, it is preferable to control changes to the artificial motion intraoperatively to adjust for anatomical conditions.

SUMMARY OF THE INVENTION

In accordance with the present invention, there is provided an artificial intervertebral disc including housing members having spaced inner surfaces facing each other and oppositely facing outer surfaces for engaging spaced apart vertebral surfaces. Bearing surfaces extend from each of the inner surfaces for engaging each other while allowing for low friction and compression resistant movement of the housing members relative to each other while under compression. Load sharing pads disposed between the inner surfaces and about at least a portion of the bearing surfaces share absorption of compressive loads with the bearing surfaces while controllably limiting the relative movement of the housing members.

The present invention further provides a method of assembling an artificial intervertebral disc in vivo by inserting upper and lower housing members into an intervertebral space and disposing cushioning pads between the inner surfaces of the housing members, placing the pads in compression. A pair of disc members are inserted between the inner surfaces of the plates, the disc members having abutting low friction surfaces therebetween. The disc members effectively are surrounded by the pads whereby the disc members and pads are under compressive forces.

Additionally, a method of separating opposing vertebrae at an intervertebral space includes the steps of engaging artificial bearing surfaces between the intervertebral spaces while allowing low friction and compression resistant movement of the bearing surfaces relative to each other, sharing absorption of the compressive forces with at least one load bearing pad disposed about at least a portion of the bearing surfaces, and limiting the relative movement of the bearing surfaces.

DESCRIPTION OF DRAWINGS

Other advantages of the present invention can be readily appreciated as the same becomes better understood by reference to the following detailed description when considered in connection with the accompanying drawings wherein:

FIG. 3 is a side perspective view of a second embodiment of the present invention;

FIG. 4 is a perspective view of a lower disc constructed in accordance with the present invention;

FIG. 5 is a side view of an upper disc constructed in accordance with the present invention;

FIG. 6 is a top perspective view of an upper housing member made in accordance with the present invention;

FIG. 7 is a top plan view of a lower housing member made in accordance with the present invention;

FIG. 8 is a side perspective view of a third embodiment of the present invention;

FIG. 9 is a perspective view of the present invention with the top housing member removed;

FIG. 10 is a perspective view of an alternative pad configuration of the present invention;

FIG. 11 is a perspective view of a further alternative embodiment of the pad member;

FIG. 12 is a further alternative embodiment of the present invention;

FIG. 13 is an exploded side perspective view of the embodiment shown in FIG. 12;

DETAILED DESCRIPTION OF THE INVENTION

Figure 1:
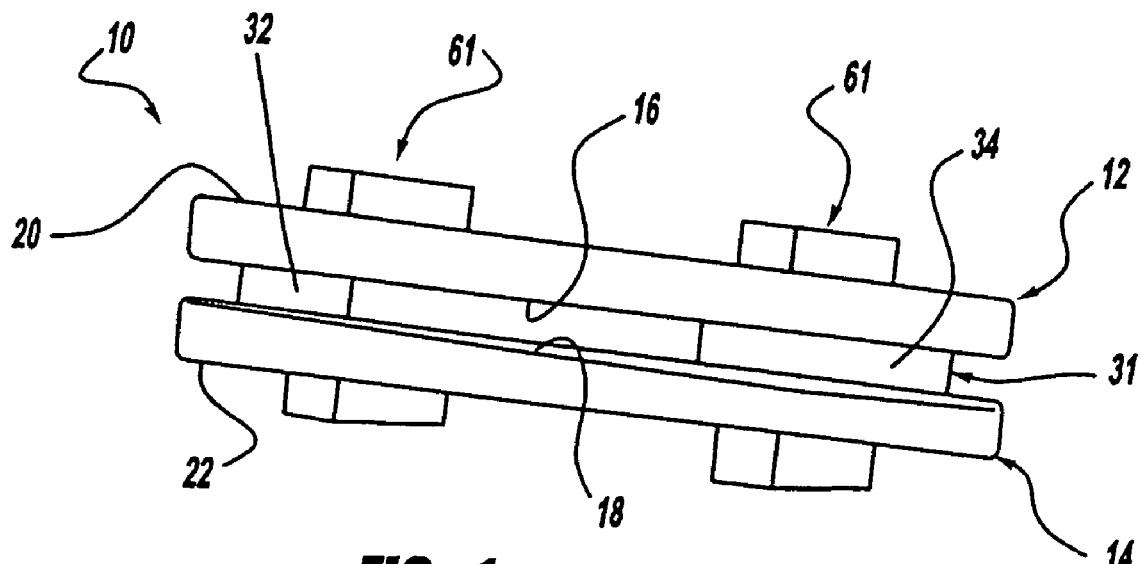
FIG. 1 is a side perspective view of a preferred embodiment of the present invention.

An artificial intervertebral disc constructed in accordance with the present invention is generally shown at 10 in the figures. Like structures of various embodiments are indicated by primed numerals in the Figures. The invention is an artificial intervertebral disc, sometimes referred to by other terminology in the prior art such as intervertebral spacer device, or spinal disc for replacement of a damaged disc in the spine. The invention restores motion to the damaged natural disc that allows for motion as well as cushioning and dampening. As described below in more detail, the present invention also allows changes to the artificial disc motion intraoperatively to adjust for specific anatomical conditions.

Referring to the Figures, the disc 10 includes an upper housing member generally shown at 12 and a lower housing member generally shown at 14. The housing members 12, 14 include spaced inner surfaces 16 and 18 facing each other and oppositely facing outer surfaces 20, 22 for engaging spaced apart vertebral surfaces. A pair of bearing surfaces 24, 26 extend from each of the inner surfaces 16, 18 for engaging each other while allowing for low friction and compression resistant movement of the housing members 12, 14 relative to each other while under compression. As shown in the various Figures, the bearing surfaces are integral with disc members 28, 30. Alternatively, the bearing surfaces 24, 26 can be surfaces on projections that are integral with and extend from the housing members 12, 14, per se. The housing members 12, 14 can be made from various materials including metals, such as titanium, as well as ceramics, and plastics. If integral with the bearing surfaces 24, 26, the housing members 12, 14 can be made from the preferred material for the bearing discs 28, 30 as discussed above. Based on this teaching, various other configurations can be made by those skilled in the art incorporating the present invention.

The upper and lower bearing surfaces 24, 26 engage each other when disposed correctly opposite each other. The configuration creates a three-dimensional bearing surface. As discussed below, the bearing surfaces 24, 26 are disposed on noncompressible discs or the like, thereby providing structure for absorbing compressive loads placed on the outer surfaces 20, 22 of the housing members 12, 14.

Figure 2:
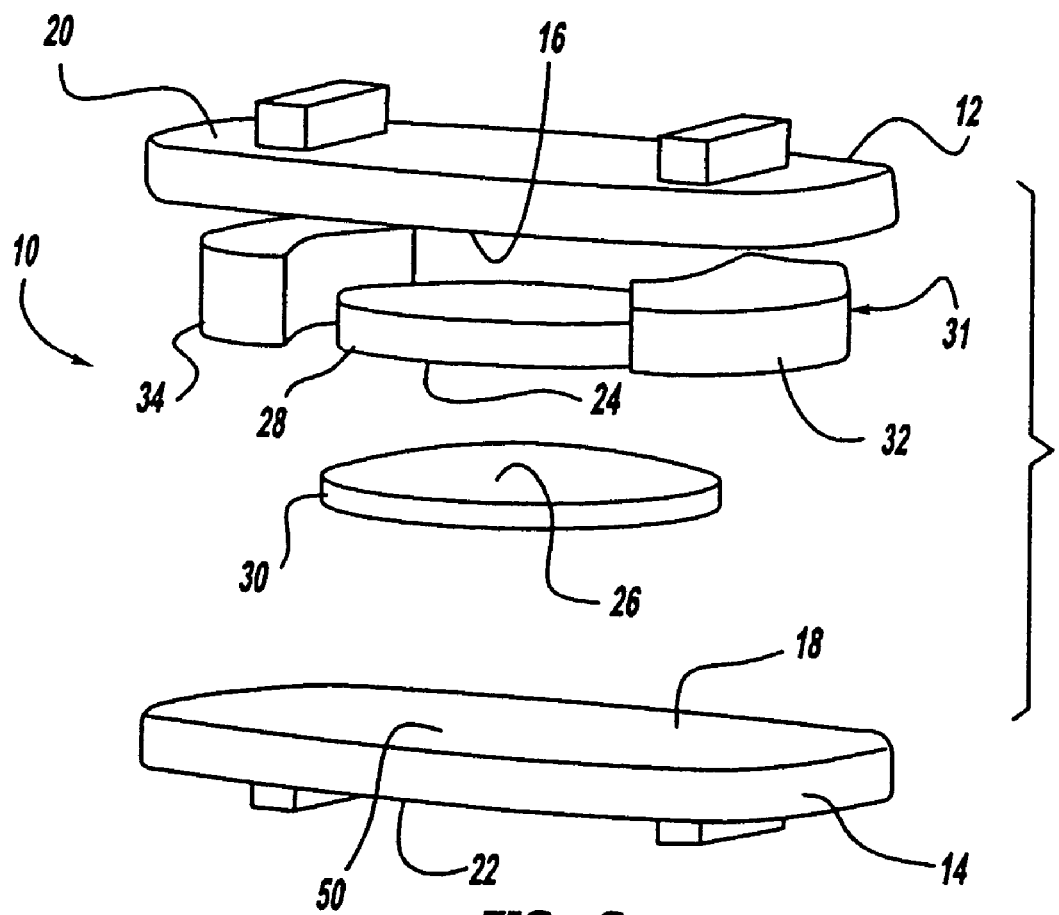
FIG. 2 is a side exploded view of the embodiment shown inn FIG. 1.

Load sharing pads generally shown at 31 and specifically indicated as pads 32 and 34 in FIGS. 1 and 2 are disposed between the inner surfaces 16, 18 and about at least a portion of the bearing surfaces 24, 26 for sharing absorption of compressive loads with the bearing surfaces 24, 26 while limiting relative movement of the housing members 12, 14. More specifically, under in vivo loading conditions, the centralized bearing surfaces 24, 26 not only provide for three-dimensional movement relatively between the housing members 12, 14, but also share with the load sharing pads 32, 34 the function of distributing compressive loads on the device 10 to provide a system for motion and effective load distribution. The centralized low friction and compression resistant bearing surfaces 24, 26 allow full motion in multiple planes of the spine while the load distributing damper and cushioning pads 32, 34 simultaneously share the load. Critical is the function of the pads 32, 34 sharing the load with the bearing surfaces 24, 26. Although the pads 32, 34 can be compressible, the compression is limited by the noncompressibility of the bearing surfaces 24, 26. Likewise, although the bearing surfaces allow for motion in multiple planes, the pads 32, 34 are fixedly secured to the housing members 12, 14, thereby allowing for a degree of flexibility and therefore movement of the housing members 12, 14 relative to each other, yet limiting such movement. In total, each element, the bearing surfaces 24, 26, and pads 32, 34, allow for movement, yet limit such movement, whether it is the sliding movement of the bearing surfaces 24, 26 or the cushioning movement allowed by the pads 32, 34. Each element allows for relative movement, yet each element limits the movement of the other element of the system.

In view of the above, the system allows restoration of normal motion while maintaining load cushioning capabilities of a healthy disc. This is particularly apparent with motion of the spine. Any rotation of the upper and lower housing members 12, 14 causes the load distributing dampening and cushioning pads 32, 34 to absorb some of the load.

As shown in the various figures, the bearing surfaces 24, 26 can include a concave surface portion on one of the upper or lower disc members 28, 30, and a convex surface portion on the other. The concave surface is seated within the convex surface for sliding movement relative thereto effectively resulting in relative pivoting motion of the housing members 12, 14, which compresses at least a portion of the load sharing pads 32, 34 while extending at least a portion of the oppositely disposed load bearing pad 32, 34. Alternatively, either one of the top and bottom disc members 28, 30 can have either of the convex or concave surfaces.

The disc members 28, 30 can be made from a composition that is noncompressible. Such compositions can be selected from the group including ceramics, plastics, and metal bearing materials, such as cobalt and chrome. Alternatively, the housing members 12, 14 can include projections wherein the disc members 28, 30 are effectively integral with the housing members 12, 14. In this situation, the entire housing, including the projections having the bearing surfaces 24, 26 thereon, can be made from the noncompressible material, preferably a ceramic. As stated above, alternative configurations can be made by those skilled in the art once understanding the present invention.

The load sharing pads 32, 34 can be in various configurations shown in the Figures, such as paired pads 32, 34 shown in FIGS. 1-3. Alternatively, the device 10 can include four oppositely disposed pads 38, 40, 42, 44 as shown in FIG. 10. A further embodiment of the invention is shown in FIG. 11, wherein a single pad 46 substantially covers the surface 18'''' of the housing member 14''''. The pads can contour to the shape of the housing members such as shown in FIGS. 12, 13, wherein the pad member 48 is an annular pad member disposed with a annular housing 12''''', 14'''''. The selection of such housing members 12, 14 and pad members 31 can be determined based on the location of the placement of the device 10 as well as the spacing conditions between the vertebrae and load bearing necessities depending on the level of the spine being addressed. In other words, different shaped devices, such as the round shaped housing members shown in FIG. 12 can be used for placement between smaller discs, such as cervical spines whereas more rectangular shapes, such as the housing members shown in FIGS. 1-11 can be used in between lumbar vertebrae.

The load sharing pads 31, in which ever shape they are configured, are elastic for allowing relative twisting movement between the housing members 12, 14 effecting relative three-dimensional movement between the housing members 12, 14, while limiting the movement and preventing contact between the housing members 12, 14 except for the contact between the bearing surfaces 24, 26. By elastic, it is meant that the pad members 31 are compressible and stretchable, yet provide a self centering effect on the assembly with specific regard to the housing members 12, 14, as well as the bearing surfaces 24, 26. Deflection or rotation of the forces created due to relative movement of the bearing surfaces 24, 26, and likewise the housing members 12, 14, forces the pads 31 to act in such a way to counter the force, thus allowing a unique self-centering capability to the assembly 10. While in an ideal situation, wherein the patient's facets are uncompromised and ligamental balances are intact, this self-centering aspect may not be completely necessary. In other words, the patient's anatomy may still provide stabilization and specifically, ligaments may provide self-centering. However, ligamental imbalance, and damaged facets would normally make an artificial disc questionable, at best, with use of the current technology that is available. In such cases, having the ability to self-center and restrict motion (the pads 31 of the present invention are elastic and thus restrict motion by stretching and returning to rest), the possibility of extending indications to patients currently considered outside of the scope of artificial disc technology will be highly advantageous.

The pads 31 of the present invention provide further advantages to the invention. A key advantage is the ability to adjust the pads 31 to patient and surgeon requirements. In such cases wherein range of motion needs to be restricted due to compromised facets, a harder, less elastic pad can be inserted between the housing members 12, 14. Since this less elastic pad would move and stretch less, the disc would be automatically restricted in motion. This method of adjusting pads can be done intraoperatively to compensate for surgical and patient conditions. To one skilled in the art, one can fine-tune the assembly 10 to a patient's and surgeon's needs with multiple pads of different properties or materials.

The pads 31 are made from a polymer or elastomer that allows deflection under load. Examples of such polymers and elastomers are silicone, polyurethane, and urethane composites. As discussed above with regard to flexibility or elasticity, the content and composition of the pads 31 are adjustable. A highly dense material creates a very rigid disc, while a very soft material creates a very free moving disc. The motion would be restricted in all planes of the pad depending upon these factors. Rotation is also restricted, as well as flexion or movement of the disc. The amount of compression possible is restricted or allowed according to the pads material properties. This is true of motion towards the back or side-to-side motion. Thus, the pads 31 are always in contact and always share the load, under any adjustment of relative positioning of the housing members 12, 14. Since motion forces the pads to be in contact, the pads 31 automatically damper loads imposed by the artificial disc construct 10.

With specific regard to the flexibility or elasticity of the polymer or elastomer composition of the pads 31, the pads can be selected from a composition having a durometer from 20 to 98 on the Shore OO Scale. Alternatively, the pads 31 can be selected from a composition having a durometer from 10 to 100 on the Shore A Scale. A further alternative is for the pads 31 to be selected from a composition having a durometer from 22 to 75 on the Shore D Scale. In any event, the pad members 31 can be selected during the operation and procedure by the clinician to suit a specific situation. Although the pad members 31 can be pre-inserted between the housing members 12, 14 prior to insertion of the device 10 in situ, the various configurations of the present invention can allow for in situ replacement of the pad members 31 so as to custom select the flexibility or elasticity of the members. In this manner, the pad members 31 are custom designed for the individual environment of the intervertebral space into which the device is being disposed.

The disc members 28 and 30, and pads 31 can be contained or locked in position in between the housing members 12, 14 by various means. The disc 28, 30 can be locked to the housing members 12, 14 by a press fit taper, retaining ring, or other means. The key aspect of such locking mechanisms is to prevent the disc members 28, 30 from moving against the upper or lower housing members 12, 14 once installed in order to prevent additional wear.

FIGS. 1 and 2 show disc members 28, 30 disposed in recesses (only the lower recess 50 is shown in FIG. 2 in an exploded view) in each of the inner surfaces 16, 18 of the housing members 12, 14. FIGS. 6 and 7 show plan views of a second embodiment of the housing member 12', 14', wherein each recess 50', 52 includes a ramped surface 54, 56 leading from an outer edge to the inwardly tapered recess portion 50', 52. The ramping 54, 56 allows access of the disc members 28,30 in between the housing members 12', 14' after placement of the housing members 12', 14' in the intervertebral space. This intraoperative access of the disc members 28, 30 allows the surgeon to test different size disc members under load conditions to perfectly fit the disc members in place. Such an advantage is not obtainable with any prior art device.

Figure 16:
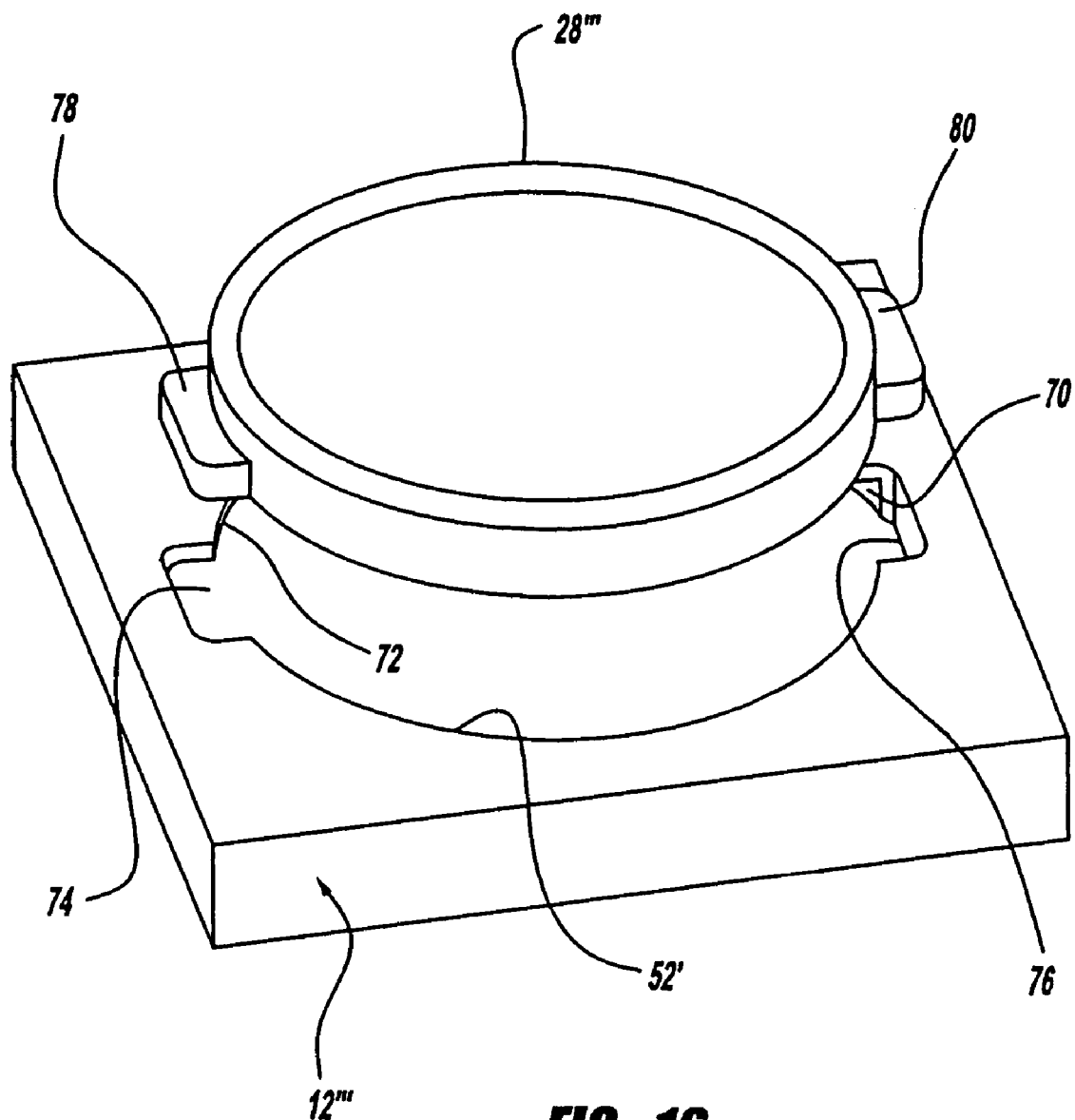
FIG. 16 is an exploded view of a further embodiment of the present invention demonstrating a bayonet type locking of a disc member to a housing member.
Figure 17:
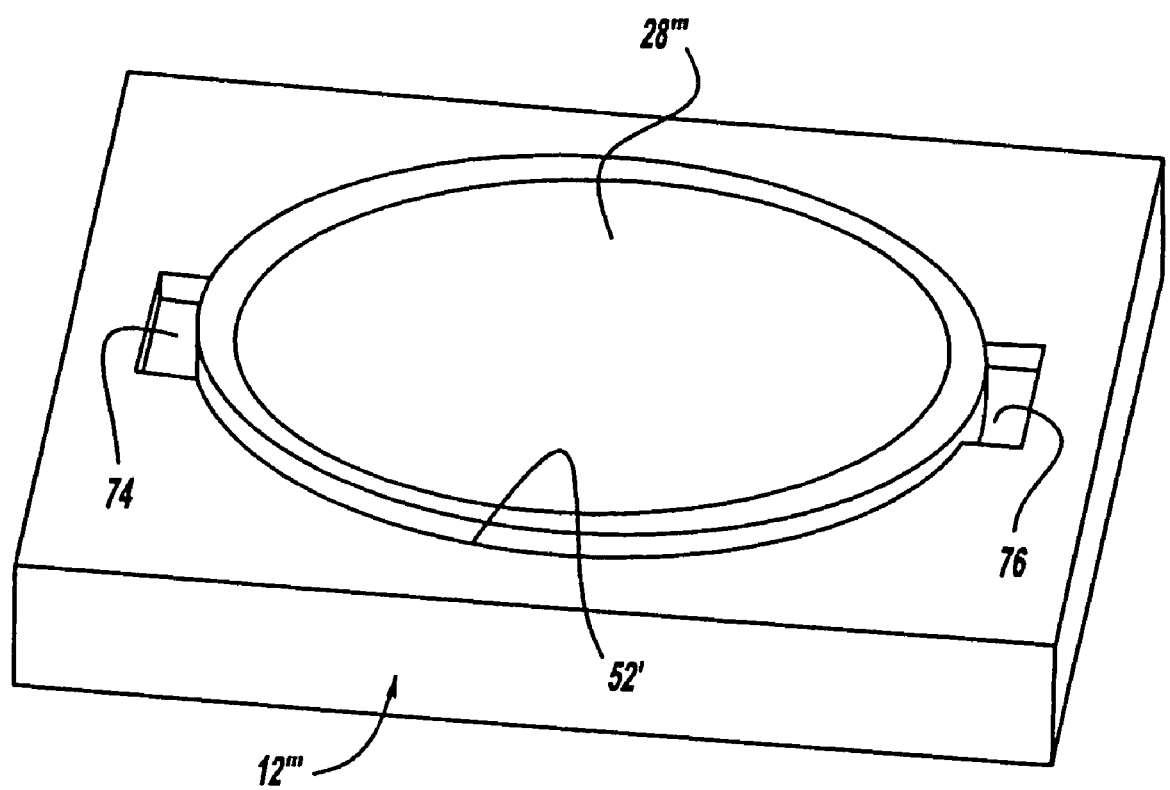
FIG. 17 is a perspective view of the disc member utilizing the bayonet locking mechanism to lock the disc member within a housing member.

An alternative mechanical mechanism for locking the disc members within the housing members are shown in FIG. 16. The representative housing member 12''' includes recess 52'. The recess 52' includes a substantially arcuate peripheral undergroove 70. The groove is defined by a lip portion 72 including at least one and preferably at least two openings 74, 76. The disc member 28''' includes bayonet style flanges 78, 80 extended radially outwardly therefrom, the flanges 78, 80 being shaped so as to be received through recess 74, 76. In operation the disc member 28''' can be disposed within the recess 52' such that the flanges 78, 80 align with recesses 74, 76. Once the disc member 28''' can be rotated thereby providing a bayonet style locking mechanism of the disc member 28''' within the housing 12''', as shown in FIG. 17.

Figure 18:
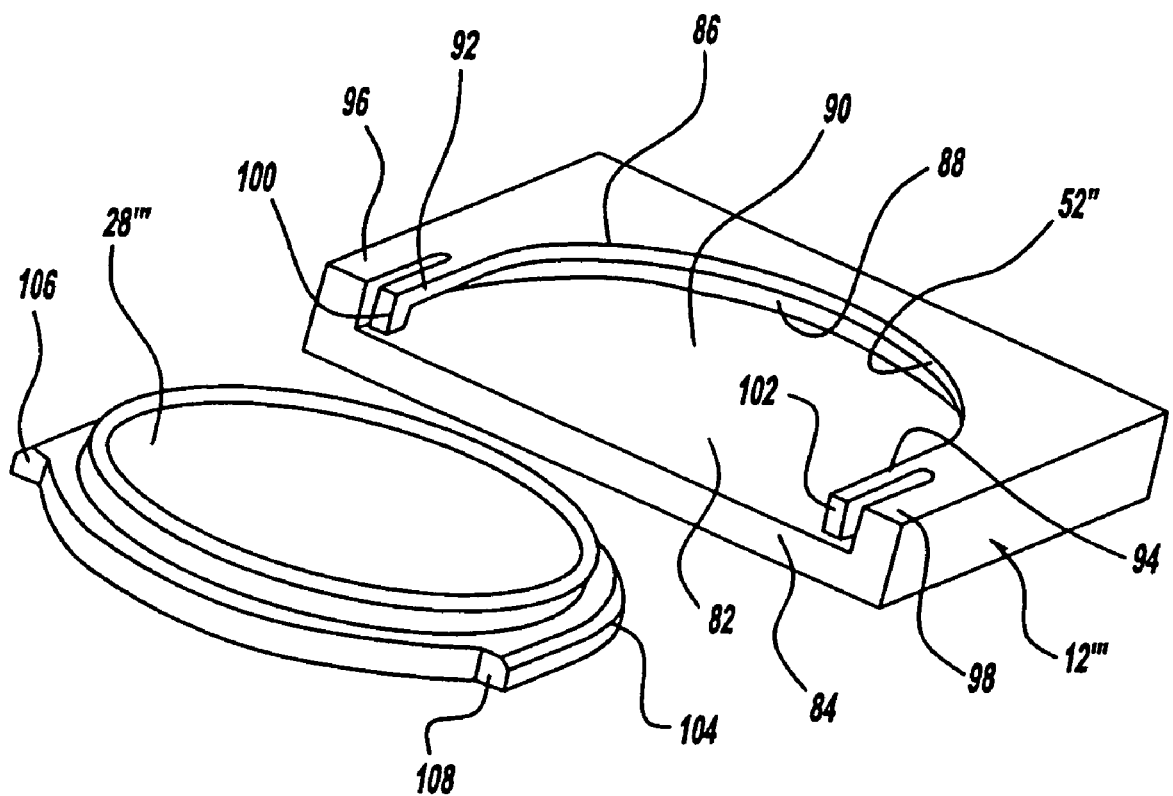
FIG. 18 is an exploded view of a disc member and housing member showing a further embodiment of a locking mechanism for locking the disc member within the housing member.
Figure 19:
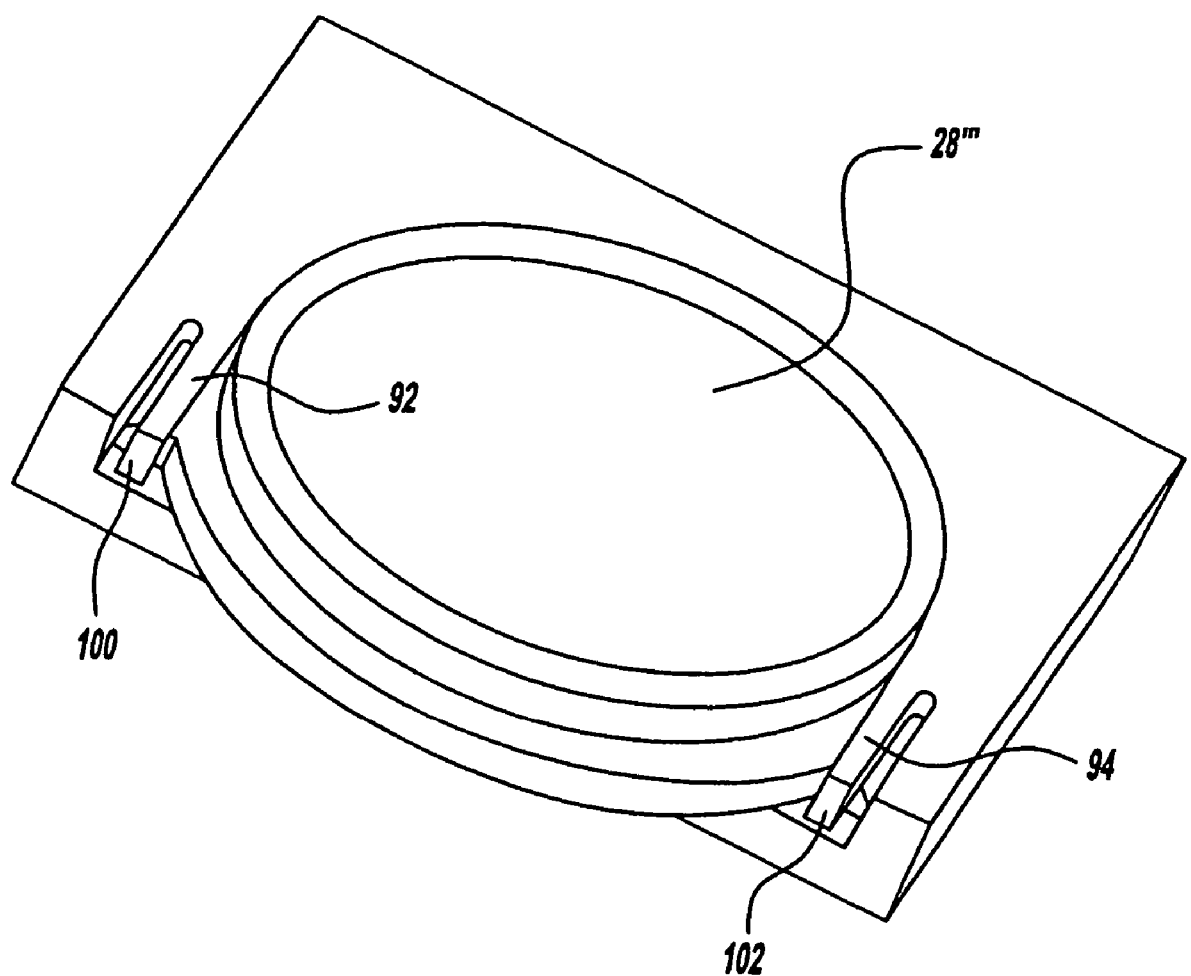
FIG. 19 is a perspective view showing the disc member locked within the housing member.

A further alternative embodiment of the locking mechanism is shown in FIGS. 18 and 19. The housing member 12''' includes a substantially arcuate recess 52'' having an open end portion 82 extending to an edge 84 of the housing member 12'''. The recess 52'' includes a lip portion 86 extending about a substantial portion thereof defining an inner groove 88 between the seating surface 90 of the recess 52'' and the lip portion 86. Arm portions 92, 94 are extensions of the lip portion 86 but extend from and are separate from peripheral ends 96, 98 of the housing member 12'''. The arm portions 92, 94 have a spring-like quality such that they can be deflected outwardly from the arcuate circle defined by the recess 52''. Each of the arms 92, 94 has an elbow portion 100, 102 extending from each arm portion 92, 94 towards the seating surface 90, respectively. The disc member 28''' includes a substantially arcuate peripheral, radially outwardly extending flange portion 104. The flange portion 104 includes two abutment edges 106, 108. In operation, the flange 104 and disc member 28''' are disposed within the annular recess or groove 88, deflecting outwardly the arms 92, 94. Once disposed in the recess 52'', as shown in FIG. 19, the elbows 100, 102 engage the abutment surfaces 106, 108 of the disc member 28''' thereby locking the disc member 28''' in place. Outward deflection of the arms 92, 94 can selectively release the disc member 28''' from locked engagement to provide for further adjustment of the selection of the disc member during an operation procedure.

Also, as best shown in FIGS. 6 and 7, the pads members 31 can be disposed in recesses 58, 60 in the lower and upper housing members 12', 14' respectively. It is preferable to permanently adhere the pad members 31 to the housing members 12', 14' by use of mechanical mechanisms and/or various adhesives, such as cyanoarylates, urethanes, and other medical grade adhesives. This list of adhesives, as with other listings of ingredients in the present application, is merely exemplary and not meant to be exhaustive.

Examples of mechanical mechanisms for locking the pad members 31 into recesses in the housing members are shown in FIGS. 20-23. One such mechanism is an undercut locking mechanism shown in FIGS. 20-22. Housing member 12'''' includes a central recess 52 such as shown in FIG. 6 having a ramp portion 56. The ramp portion 56 includes a centrally located tongue groove 57 allowing for the insertion of a spatula type device under a disc member disposed within the recess 52 for releasing the disc member from the recess, similar to the use of a shoehorn type mechanism. Recesses 60' include undercut recesses 110, 112 for locking engagement with a peripheral flange portion 114 extending from an edge 116 of a pad member 31'. Since the pad member is made from a deflectable material, the flange portion 114 can be force-fit into and seated within the undercut 110, 112. The undercut locking mechanism effectively prevents the pad member 31' from disengagement with the housing member 12'''' in situ. Of course, the upper flange 118 would be locked within a similar undercut locking detail of recesses within the opposing housing member (not shown).

Figure 23:
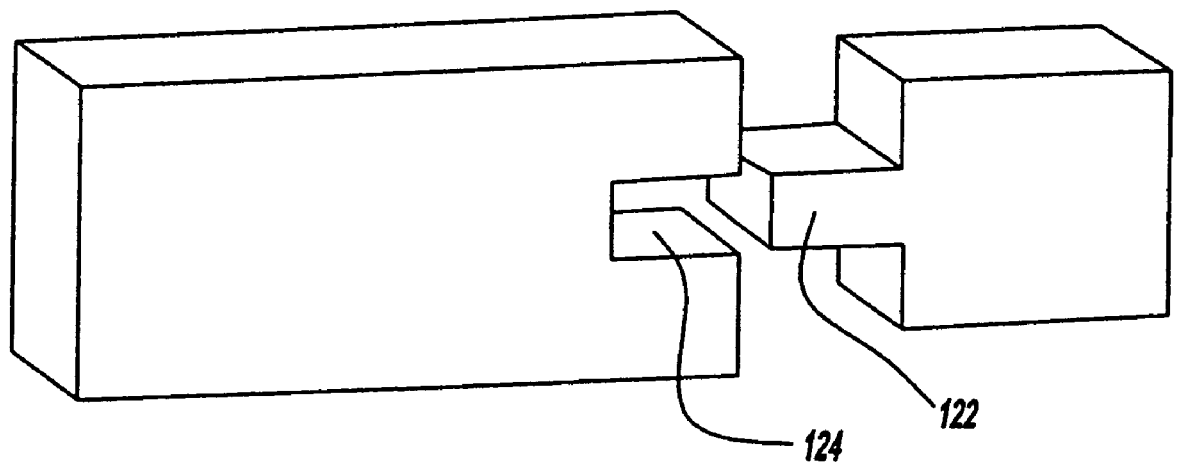
FIG. 23 shows a further embodiment of a locking mechanism made in accordance with the present invention.

An alternative locking mechanism between the pad member and housing member can be a tongue-and-groove relationship as shown in FIG. 23. Either the pad or the housing can include the tongue portion 122 and the other pad and housing members can include the groove 124. In other words, either of the locking members can include the tongue 122 and the other of the members being locked would include the groove 124. An alternative of this or the other locking mechanism shown is that the recess and/or pad can include multiple grooves or slots as well as multiple tongues.

The various recesses or pockets 50', 52, 58, 60 can be of different relative sizes and shapes. For example, the upper housing member 12' may have a larger recess or pocket for seating a relatively larger one of said discs 28 and the lower housing member 14' may be include a smaller (larger and smaller referring to diameter of the annular recess) of the recesses or pockets for seating a relatively smaller one of the lower disc 30, thereby providing for an increased range of motion at the bearing surface interface.

Figure 14:
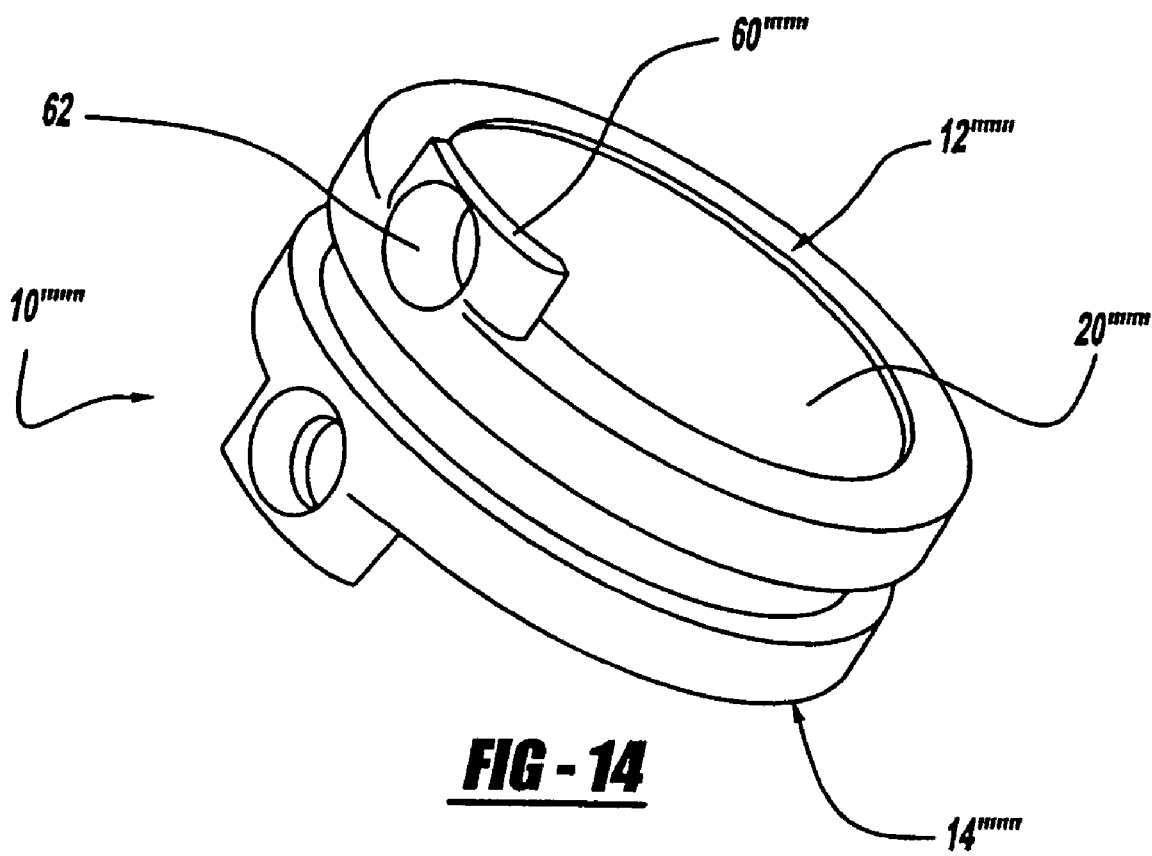
FIG. 14 shows an alternative embodiment of the housing members of the present invention.
Figure 15:
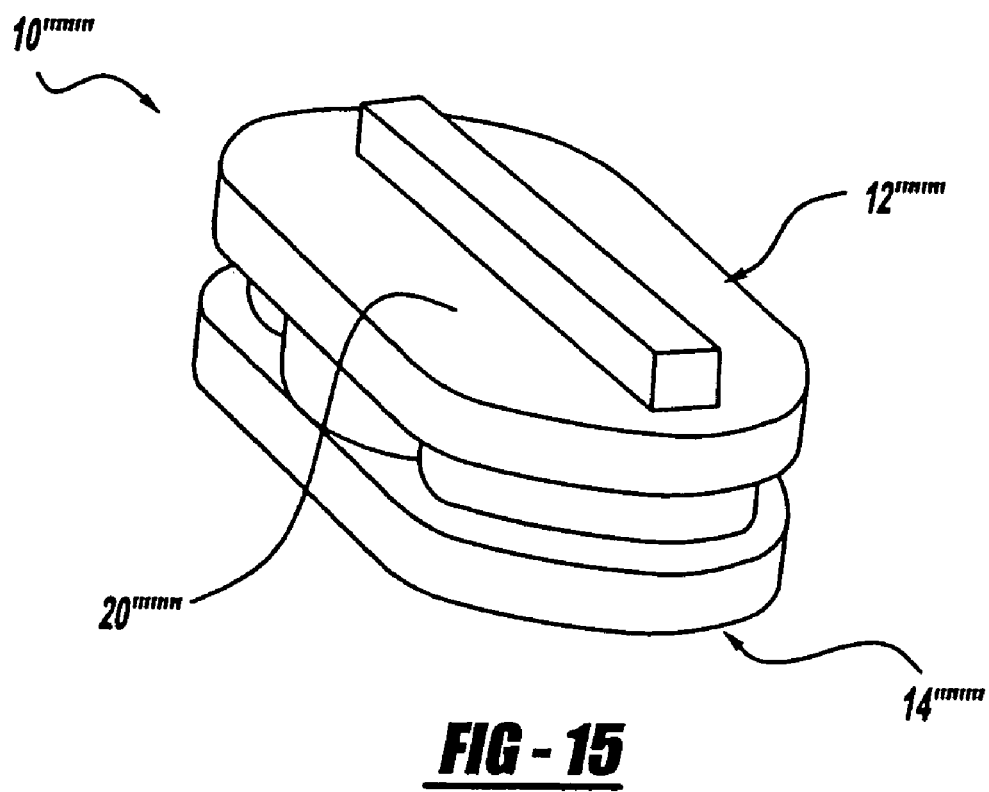
FIG. 15 shows a further alternative embodiment of the housing members of the present invention.

The various Figures show that the outer surfaces 20, 22 of the various embodiments of the housing members 12, 14 can include flanges generally indicated at 60. The flanges 60 or fins, as they are sometimes referred to in the art, provide a mechanism for fixation to the intervertebral surfaces. Various embodiments, such as those shown in FIGS. 1 and 2 are dual fin constructs. Other embodiments, such as those shown in FIGS. 8, 12, and 13 are single fin or single flange constructs. Depending upon the nature of the surfaces to which the outer surfaces 20, 22 are to abut, the surgeon can select various flange or fin configurations. Additionally, the fins 60 can be located in alternative positions, either centrally as shown in many of the Figures, or peripherally, as shown in FIG. 14, for a specific use with anterior extension plates, as with screw fixations. The flanges, such as flange 60''''' can include a bore 62 therethrough, which can be either a smooth surface or threaded depending on its intended use.

The outer surfaces 20, 22 can be smooth, which allows for easier revision as it allows for minimal to no ingrowth or they can be textured. Texturing of the outer surfaces 20, 22 allows ingrowth for long-term fixation of the assembly 10. Porous coatings, plasma spray, grit blasting, machining, chemical etching, or milling are examples of techniques for creating ingrowth capable surfaces. Coatings that enhance bone growth can also be applied. Examples of such coatings are hyroxyapatite and bone morphogenic proteins.

Figure 20:
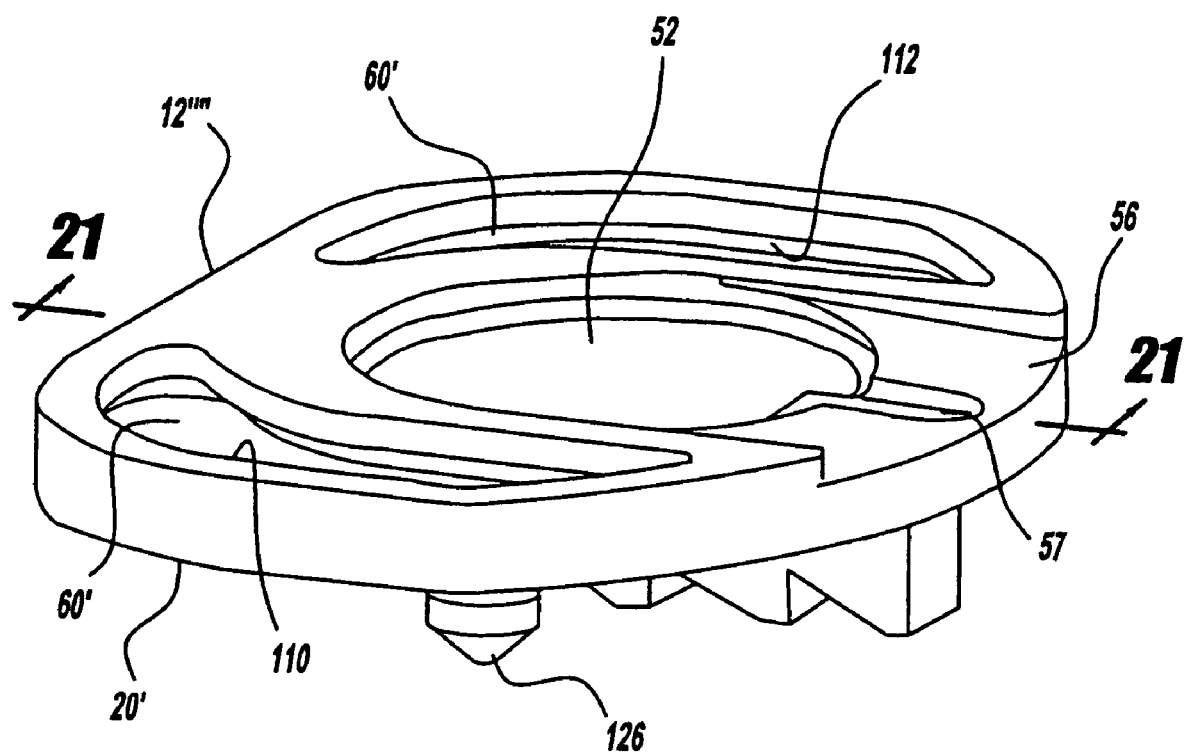
FIG. 20 is a perspective view of the a further embodiment of the housing member.
Figure 21:
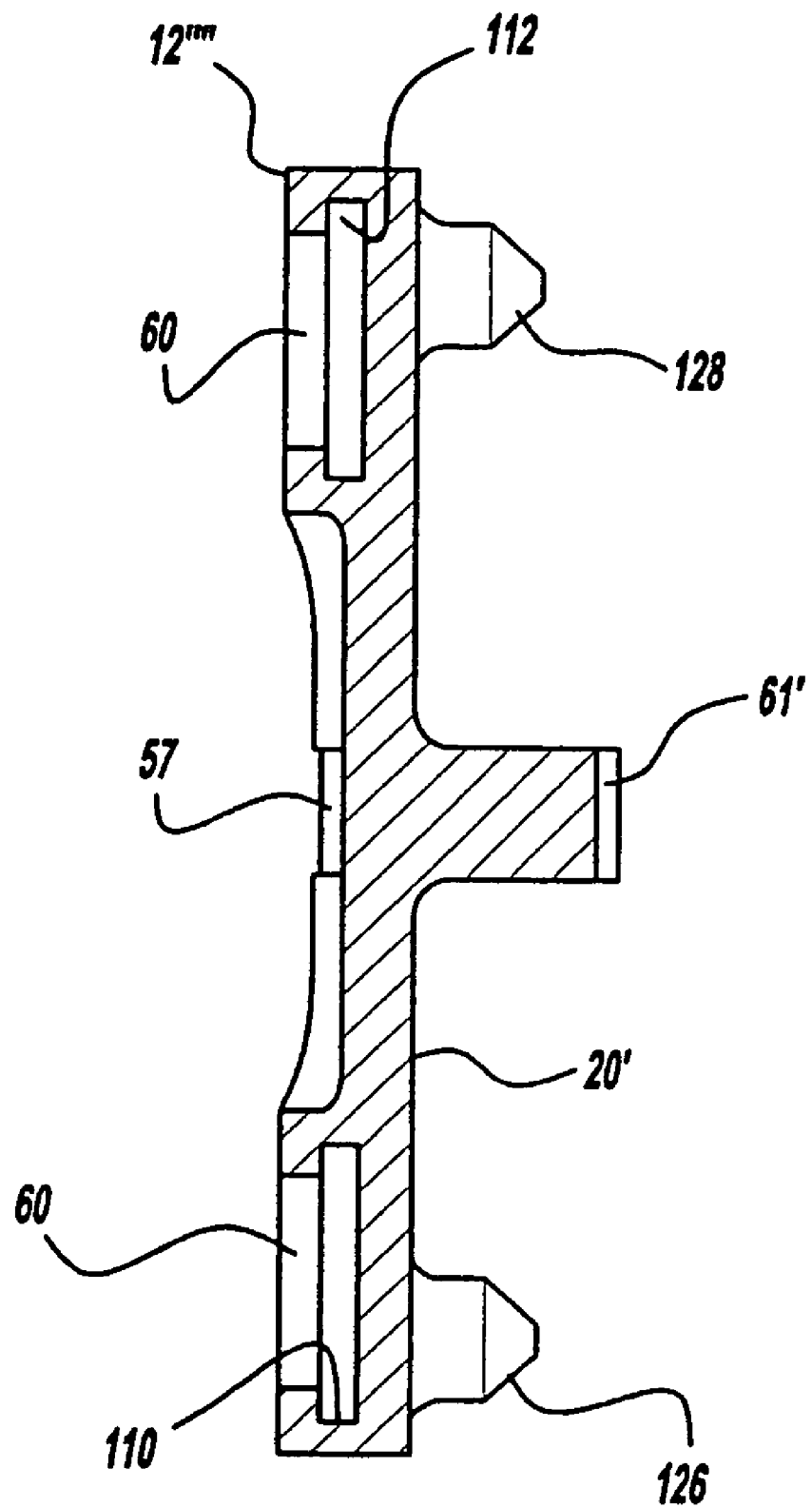
FIG. 21 is a cross sectional view taken along line 21-21 in FIG. 20.
Figure 22:
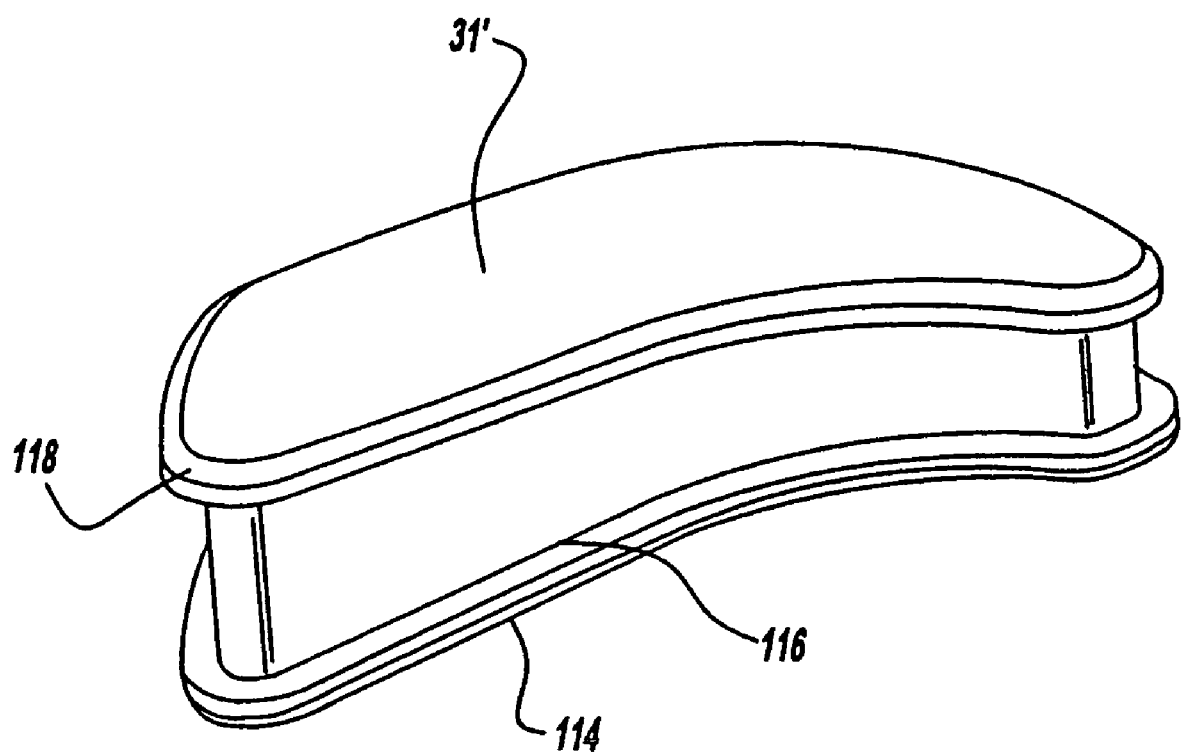
FIG. 22 is a perspective view of a load sharing pad member including flanges for locking engagement in the recesses of the housing member shown in FIGS. 20 and 21.

FIGS. 20 and 21 provide structure for further rotational stability of the device in situ. The housing member 12"" includes pointed portions 126, 128 extending from the outer surface 20' thereof. The point members 126, 128 function in conjunction with the flange portion 61' to engage an opposing vertebral surface. The point portions 126, 128 being disposed radially peripherally from the centrally disposed flange 61' provide at least a three-point engagement of the vertebral surface thereby preventing rotation of the housing member 12"" relative thereto. Of course, the point portions 126, 128 can be in made in various configurations and extend various amounts from the outer surface 20' to be custom suited to a specific vertebrae surface shape.

Various methods can be utilized for insertion of the present invention in situ. For example, an assembled device 10 as shown in FIG. 1, can be disposed between the intervertebral spaces during surgery, after calculation of space, depth, and height. Alternatively, opposing housing members 12, 14 can be disposed between the intervertebral spaces and pads 31 and disc members 24, 26 can be tested in situ prior to fixation thereof to allow for custom sizing. Accordingly, the present invention broadly provides a method of assembling an artificial intervertebral disc 10 in vivo by inserting upper and lower housing members 12, 14 into an intervertebral space and disposing cushioning pads 31 between the inner surfaces 16, 18 of the housing members 12, 14, thereby placing the pads in compression. The pair of disc members 28, 30 are inserted between the inner surfaces of the plates 16, 18. The disc members 28, 30 have abutting low friction surfaces 24, 26 therebetween. The disc members 28, 30 are surrounded by the pads 31, whereby the disc members 28, 30 and pads 31 are under compressive forces and share such compressive forces. This step of the bearing surfaces 24, 26 and shock absorbing pads 31 sharing absorption of the compressive forces and limiting the relative movement of the housing members 12, 14 is an advantage not found in the prior art.

What is claimed is:

1. An artificial intervertebral disc comprising:
   housing members including spaced inner surfaces facing each other and oppositely facing outer surfaces for engaging spaced apart intervertebral surfaces, one of the housing members having an undercut recess formed therein;
   bearing means extending from each of said inner surfaces for engaging each other while allowing for low friction and compression resistance relative to each other while under compression;
   load sharing means disposed between said inner surfaces and about at least a portion of said bearing means for sharing absorption of compressive loads with said bearing means while limiting the relative movement of said housing members, wherein said load sharing means includes a pad member disposed and retained between said inner surfaces of said housing members and having cushioning and elastic properties for countering and thereby self centering against forces caused by relative movement of said housing member while under compressive forces are applied to said outer surfaces of said housing members, the pad member including a flange extending around an external periphery thereof, the flange seated in locking engagement in the recess; and
   a pair of disc members, each of said disc members including one of said bearing means, said inner surfaces of said housing members including disc seating means for seating one of said disc members therein in opposing relationship of the other of said disc members seated in said seating means of the other of said housing members.

2. A disc according to claim 1, wherein said housing members include seating means for seating said pad members between said inner surfaces.

3. A disc according to claim 2, wherein said seating means includes at least one pocket recessed into said inner surface of said housing member for seating a portion of said pad member therein.

4. A disc according to claim 3, including adhering means for fixedly adhering said pad member within said pocket.

5. A disc according to claim 1, wherein said pad members are selected from a composition having a durometer in the range of 20 to 98 on the Shore OO Scale.

6. A disc according to claim 1, wherein said pad members are selected from a composition having a durometer of 10 to 100 on the Shore A Scale.

7. A disc according to claim 1, wherein said pad members are selected from a composition having a durometer of 22 to 75 on the Shore D Scale.

8. A disc according to claim 1, wherein the pads are made from a composition selected from the group including polymers and elastomers.

9. A disc according to claim 8, wherein the pads are made from a composition selected from the group including silicone, polyurethane, and urethane composites, plastics, polymers, and elastomers.

10. A disc according to claim 1, wherein said housing members are constructed from a composition selected from the group including metals, ceramics, and plastics.

11. A disc according to claim 1, wherein said outer surface of said housing member includes a surface texture for accepting bone growth therein.

12. A disc according to claim 11, wherein said surface texture is selected from the group including physically roughened, porous coated, and plasma coated surfaces.

13. A disc according to claim 11, further including bone growth inducing means disposed on said outer surface of said housing member for increasing bone growth on the said outer surface.

14. A disc according to claim 11, wherein said bone growth inducing means is a coating selected from the group including hyroxyapatite and bone morphogenic proteins.

15. A disc according to claim 1, wherein said load sharing means consists of a unitary pad member disposed about said bearing means and separating substantially all of the reminder of said inner surface.

16. A disc according to claim 1, wherein said load sharing means includes at least two pad members disposed peripherally relative to said bearing means and between said inner surfaces.

17. A disc according to claim 1, including at least one flange extending from said outer surface for fixing said housing members to a vertebral surface.

18. A disc according to claim 1, wherein at least one of said outer surfaces includes a recessed portion.

19. A disc according to claim 18, further including a porous coating disposed within said recess.

20. An artificial intervertebral disc comprising:
   housing members including spaced inner surfaces facing each other and oppositely facing outer surfaces for engaging spaced apart intervertebral surfaces, each of the housing members having a recess formed therein;
   a pair of disc members, one of said disc members including a concave bearing surface and the other of said disc members including a convex bearing surface, said inner surfaces of said housing members including disc seating means for seating one of said disc members therein in opposing relationship of the other of said disc members seated in said seating means of the other of said housing members; and load sharing means disposed between said inner surfaces and about at least a portion of said bearing means for sharing absorption of compressive loads with said bearing surfaces while limiting the relative movement of said housing members, wherein said load sharing means includes a pad member having a flange extending around an external periphery thereof, the pad member being disposed and retained between said inner surfaces of said housing members the flange seated in locking engagement in one of the recesses, and the pad member having cushioning and elastic properties for countering and thereby self centering against forces caused by relative movement of said housing members while under compressive forces are applied to said outer surfaces of said housing members.

21. An artificial intervertebral disc comprising:

housing members including spaced inner surfaces facing each other and oppositely facing outer surfaces for engaging spaced apart intervertebral surfaces, each of the housing members having a plurality of recesses formed therein;

a plurality of load sharing pads disposed between said inner surfaces and about at least a portion of said bearing means for sharing absorption of compressive loads with said bearing means while limiting the relative movement of said housing members, each of the load sharing pads including a flange extending therefrom, wherein each flange is seated in locking engagement in one of the recesses, wherein said load sharing pads have cushioning and elastic properties for countering and thereby self centering against forces caused by relative movement of said housing members while under compressive forces are applied to said outer surfaces of said housing members; and a pair of disc members, one of said disc members including a concave bearing surface and the other of said disc members including a convex bearing surface, said inner surfaces of said housing members including disc seating means for seating one of said disc members therein in opposing relationship of the other of said disc members seated in said seating means of the other of said housing members.

22. An artificial intervertebral disc comprising:

a first housing member having:
   a first outer surface for engaging a first intervertebral surface; and
   a first inner surface having a central recess and a plurality of side recesses formed therein;

a second housing member having:
   a second outer surface for engaging a second intervertebral surface; and
   a second inner surface having a central recess and a plurality of side recesses formed therein, the second inner surface facing the first inner surface;

a first disc member having:
   a first disc seating surface disposed in the central recess of the first housing member; and
   a concave bearing surface;

a second disc member having:
   a second disc seating surface disposed in the central recess of the second housing member; and
   a convex bearing surface in sliding engagement with the concave bearing surface; and a pair of load sharing pads symmetrically arranged with respect to the first and second disc members, the first and second disc members being disposed between the load sharing pads, each load sharing pad having:
   a first surface disposed in a side recess in the first housing member;
   a second surface disposed in a side recess in the second housing member;
   a concave side surface facing the first and second disc members; and
   a convex side surface facing away from the first and second disc members.

* * * * *